United States Patent
Takayama et al.

(10) Patent No.: US 12,312,577 B2
(45) Date of Patent: May 27, 2025

(54) ACCOMMODATION CASE, ACCOMMODATION CASE STACK, AND METHOD OF OPERATING MICROFLUIDIC DEVICE

(71) Applicant: FUJIFILM CORPORATION, Tokyo (JP)

(72) Inventors: Hidetoshi Takayama, Kanagawa (JP); Koju Ito, Kanagawa (JP); Takahiro Oba, Kanagawa (JP); Keisuke Oku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 908 days.

(21) Appl. No.: 17/462,024

(22) Filed: Aug. 31, 2021

(65) Prior Publication Data

US 2021/0395673 A1    Dec. 23, 2021

Related U.S. Application Data

(63) Continuation of application No. PCT/JP2020/002932, filed on Jan. 28, 2020.

(30) Foreign Application Priority Data

Mar. 12, 2019    (JP) .................... 2019-044497

(51) Int. Cl.
*C12M 1/00*     (2006.01)
*C12M 3/06*     (2006.01)
(Continued)

(52) U.S. Cl.
CPC ............ *C12M 43/08* (2013.01); *C12M 23/16* (2013.01); *H02J 50/005* (2020.01); *H02J 50/10* (2016.02); *H02J 50/70* (2016.02)

(58) Field of Classification Search
CPC ......... B01L 2200/141; B01L 2200/142; B01L 2200/025; B01L 2200/147; B01L 1/025;
(Continued)

(56) References Cited

U.S. PATENT DOCUMENTS

2002/0114739 A1    8/2002    Weigl et al.
2007/0236174 A1    10/2007   Kaye
(Continued)

FOREIGN PATENT DOCUMENTS

JP    2009-111557 A    5/2009
JP    2013-132134 A    7/2013
(Continued)

OTHER PUBLICATIONS

International Search Report issued in International Application No. PCT/JP2020/002932 on Mar. 17, 2020.
(Continued)

*Primary Examiner* — Kathryn Elizabeth Limbaugh
(74) *Attorney, Agent, or Firm* — SOLARIS Intellectual Property Group, PLLC

(57) ABSTRACT

There is provided an accommodation case (1) having a first wall part (33) in which a power supply unit (40) that transmits electric power to a power supply destination in a noncontact state is provided, a second wall part (34) in which a power reception unit (50) that receives electric power that is supplied from a power supply source in a noncontact state is provided, where the second wall part (34) faces the first wall part (33), and an accommodation space (35) that is surrounded by a plurality of wall parts including the first wall part (33) and the second wall part (34).

8 Claims, 7 Drawing Sheets

(51) Int. Cl.
  *H02J 50/00* (2016.01)
  *H02J 50/10* (2016.01)
  *H02J 50/70* (2016.01)

(58) Field of Classification Search
  CPC ......... B01L 2300/023; B01L 2300/046; B01L 3/502715; B01L 9/527; C12M 43/08; C12M 23/16; G01N 2035/00455; H02J 50/005; H02J 50/10; H02J 50/502; H02J 50/70
  See application file for complete search history.

(56) References Cited

U.S. PATENT DOCUMENTS

| | | | |
|---|---|---|---|
| 2012/0235567 | A1 | 9/2012 | Karalis et al. |
| 2012/0279172 | A1* | 11/2012 | Chan .................. B65D 25/101 422/547 |
| 2013/0285477 | A1 | 10/2013 | Lo et al. |
| 2013/0312450 | A1 | 11/2013 | Iwasa et al. |
| 2015/0357833 | A1* | 12/2015 | Maekawa ............. B60L 53/305 307/104 |
| 2016/0056664 | A1 | 2/2016 | Partovi |
| 2016/0111886 | A1 | 4/2016 | Sherman et al. |
| 2017/0211875 | A1 | 7/2017 | Lee et al. |
| 2017/0279294 | A1 | 9/2017 | Fujii |
| 2018/0269720 | A1 | 9/2018 | Yoshizawa |
| 2019/0351088 | A1* | 11/2019 | Gruenbacher .......... A61L 9/122 |
| 2021/0000395 | A1 | 1/2021 | Rogers et al. |

FOREIGN PATENT DOCUMENTS

| | | |
|---|---|---|
| JP | 2013-228220 A | 11/2013 |
| JP | 5922662 B2 | 5/2016 |
| JP | 2017-169365 A | 9/2017 |
| JP | 2018-153024 A | 9/2018 |
| JP | 2018-201290 A | 12/2018 |
| JP | 2020-523564 A | 8/2020 |
| WO | 2016/043135 A1 | 3/2016 |
| WO | 2016/122088 A1 | 8/2016 |
| WO | 2017/208339 A1 | 12/2017 |

OTHER PUBLICATIONS

Written Opinion of the ISA issued in International Application No. PCT/JP2020/002932 on Mar. 17, 2020.
Extended European Search Report dated Mar. 24, 2022, issued in corresponding EP Patent Application No. 20769994.3.
English language translation of the following: Office action dated Aug. 2, 2022 from the JPO in a Japanese patent application No. 2021-505574corresponding to the instant patent application. This office action translation is submitted now in order to supplement the understanding of the cited references which are being disclosed in the instant Information Disclosure Statement.

* cited by examiner

ACCOMMODATION CASE, ACCOMMODATION CASE STACK, AND METHOD OF OPERATING MICROFLUIDIC DEVICE

CROSS-REFERENCE TO RELATED APPLICATIONS

This application is a continuation application of International Application No. PCT/JP2020/002932, filed Jan. 28, 2020, the disclosure of which is incorporated herein by reference in its entirety. Further, this application claims priority from Japanese Patent Application No. 2019-044497, filed on Mar. 12, 2019, the disclosure of which is incorporated herein by reference in its entirety.

BACKGROUND

1. Technical Field

The disclosed technology relates to an accommodation case, an accommodation case stack, and a method of operating a microfluidic device.

2. Description of the Related Art

The following are known as technologies related to electric power transmission by a wireless power supply method. For example, JP2018-153024A discloses a power transmission device that wirelessly transmits electric power to a power reception device. This power transmission device includes a first power transmission coil that transmits electric power by a first transmission method, a second power transmission coil that is arranged at a position spaced apart from the first power transmission coil by a predetermined distance or more from the first power transmission coil and transmits electric power by a second transmission method, and a housing that is capable of accommodating a power reception device between a first wall part and a second wall part. The first power transmission coil is arranged on the side of the first wall part, the second power transmission coil is arranged on the side of the second wall part, and electric power is wirelessly transmitted from any one of the first power transmission coil or the second power transmission coil to the power reception device.

WO2016/043135A, discloses a charging device having a storage space for storing a plate-shaped electronic apparatus having a power reception coil mounted on the edge part thereof, and a power supply coil that is provided on a surface facing the edge part and generates an induced current in the power reception coil of the electronic apparatus stored in the storage space.

SUMMARY

By the way, a microfluidic device is a device in which a micro flow channel or a reaction container is manufactured using a microfabrication technology such as micro electro mechanical systems (MEMS) technology and is expected to be applied in a wide range of fields such as drug discovery, toxicity evaluation, organ-on-chip, body-on-chip, and analytical chemistry. In the evaluation and analysis of cells using a microfluidic device, it is considered that electric devices such as various sensors for obtaining information on cells accommodated inside the microfluidic device and a pump for feeding a liquid to the microfluidic device, and a power source for supplying electric power to these electric devices are accommodated inside the incubator, together with the microfluidic device. Further, in a case where a wireless power supply is used as a method of supplying electric power from a power source to an electric device, the number of wires in the incubator can be reduced.

The wireless power supply by a magnetic field coupling method such as an electromagnetic coupling method or a magnetic field resonance method is a method of contactlessly transmitting electric power, in which a power reception coil receives a magnetic field generated by a power transmission coil. However, since it is necessary to arrange the power reception coil in the vicinity of the power transmission coil, the degree of freedom in arranging the power reception coil in the incubator is low. Accordingly, it was also difficult to ensure a degree of freedom in arranging electric devices such as various sensors and a pump, which are operated by receiving electric power that is supplied from the power reception coil.

Further, in a case where a microfluidic device in which cells are accommodated is accommodated inside an incubator to culture the cells, it is necessary to maintain the humidity in the incubator in a relatively high state. However, in a case where electric devices such as various sensors and a pump are exposed to a high humidity environment, there is the risk of damaging electric devices.

The disclosed technology was made in consideration of the above points and aims to ensure a degree of freedom in arranging electric devices which are targets of power supply by a wireless power supply method and to suppress the risk of damaging electric devices.

An accommodation case according to the disclosed technology has a first wall part in which a power supply unit that transmits electric power to a power supply destination in a noncontact state is provided, a second wall part in which a power reception unit that receives electric power that is supplied from a power supply source in a noncontact state is provided, where the second wall part faces the first wall part, and an accommodation space that is surrounded by a plurality of wall parts including the first wall part and the second wall part.

According to the accommodation case according to the disclosed technology, it is possible to ensure a degree of freedom in arranging electric devices which are targets of power supply by a wireless power supply method and to suppress the risk of damaging electric devices.

The accommodation case preferably has a moisture-proof mechanism for preventing infiltration of aqueous moisture into the accommodation space. This makes it possible to enhance the effect of suppressing the risk of damage of the electric device.

The first wall part is arranged at the upper part of the accommodation space, and the second wall part may be arranged at the lower part of the accommodation space. As a result, in a case where a plurality of accommodation cases are stacked, electric power can be transmitted between the adjacent accommodation cases.

The power supply unit is preferably arranged at a position spaced apart from the outer edge of the first wall part, and the power reception unit is preferably arranged at a position spaced apart from the outer edge of the second wall part. As a result, it is possible to reduce the influence of the electromagnetic waves radiated from the power supply unit and the power reception unit on another power supply unit or power reception unit that is adjacent to the power supply unit and the power reception unit in the plane direction.

In the accommodation case, at least one of the plurality of wall parts may have a shielding part that shields electromagnetic waves radiated from the power supply unit and the power reception unit. As a result, it is possible to suppress the leakage of electromagnetic waves radiated from the power supply unit and the power reception unit to the outside of the accommodation case. This makes it possible to suppress a risk that the electric device that is provided outside the accommodation case malfunctions due to the electromagnetic waves radiated from the power supply unit and the power reception unit.

The accommodation case may have an access port for accessing an accommodated object that is accommodated in the accommodation space. This makes it possible to access the accommodated object from the outside of the accommodation case.

The accommodation case stack according to the disclosed technology has a configuration in which a first accommodation case and a second accommodation case are stacked. The first accommodation case and the second accommodation case each have a first wall part in which a power supply unit that transmits electric power to a power supply destination in a noncontact state is provided, a second wall part in which a power reception unit that receives electric power that is supplied from a power supply source in a noncontact state is provided, where the second wall part faces the first wall part, and an accommodation space that is surrounded by a plurality of wall parts including the first wall part and the second wall part. The first wall part of the first accommodation case and the second wall part of the second accommodation case are arranged adjacent to each other.

According to the accommodation case stack according to the disclosed technology, it is possible to ensure a degree of freedom in arranging electric devices which are targets of power supply by a wireless power supply method and to suppress the risk of damaging electric devices.

A first aspect of a method of operating a microfluidic device according to the disclosed technology is realized by using the above-described accommodation case and include accommodating an electric device that is operated by receiving electric power that is supplied from the power reception unit, in the accommodation space of the accommodation case, connecting the microfluidic device to the electric device, and arranging the accommodation case in which the electric device is accommodated and the microfluidic device in an incubator, to operate the microfluidic device.

A second aspect of the method of operating a microfluidic device according to the disclosed technology is realized by using the above-described accommodation case stack and include accommodating a first electric device that is operated by receiving electric power that is supplied from the power reception unit that is provided on the second wall part of the first accommodation case, in the accommodation space of the first accommodation case, accommodating a second electric device that is operated by receiving electric power that is supplied from the power reception unit that is provided on the second wall part of the second accommodation case, in the accommodation space of the second accommodation case, connecting a first microfluidic device to the first electric device, connecting a second microfluidic device to the second electric device, and arranging the first accommodation case in which the first electric device is accommodated, the second accommodation case in which the second electric device is accommodated, the first microfluidic device, and the second microfluidic device in an incubator, to operate the first microfluidic device and the second microfluidic device.

According to the method of operating a microfluidic device according to the disclosed technology, it is possible to ensure a degree of freedom in arranging electric devices which are targets of power supply by a wireless power supply method and to suppress the risk of damaging electric devices.

The method of operating a microfluidic device includes communicating the first electric device with the second electric device. As a result, the first electric device and the second electric device can be operated in cooperation with each other.

According to the disclosed technology, it is possible to ensure a degree of freedom in arranging electric devices which are targets of power supply by a wireless power supply method and to suppress the risk of damaging electric devices due to moisture.

BRIEF DESCRIPTION OF THE DRAWINGS

Exemplary embodiments according to the technique of the present disclosure will be described in detail based on the following figures, wherein.

DETAILED DESCRIPTION

Figure 1A:
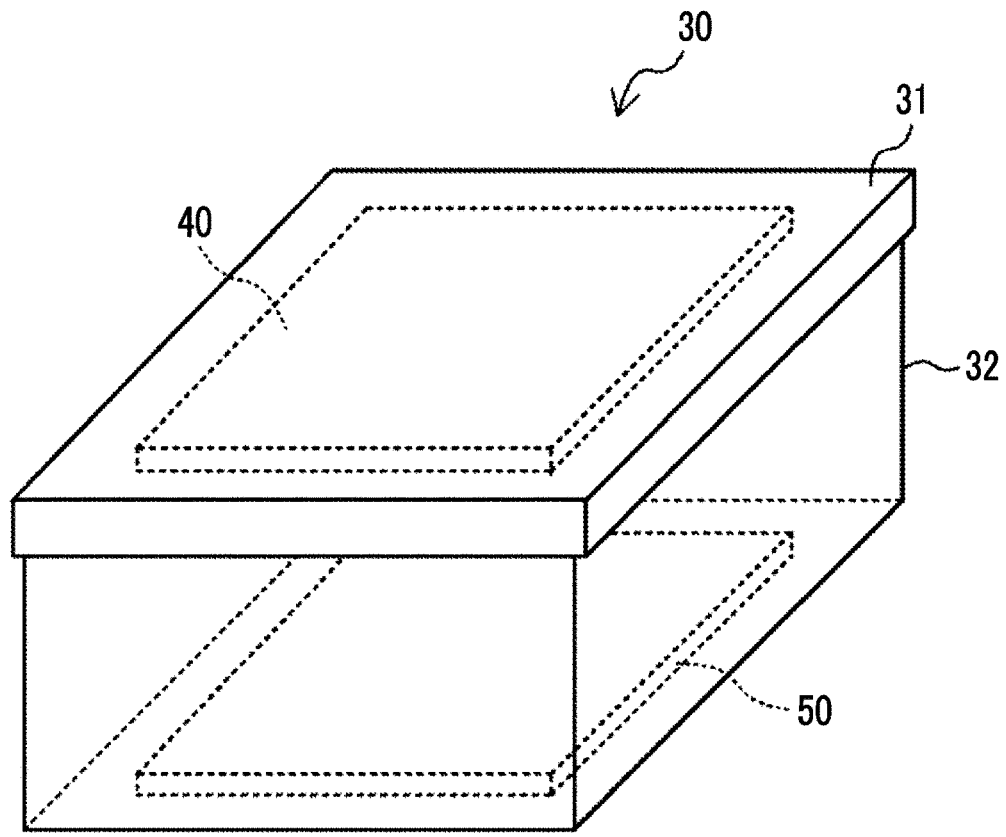
FIG. 1A is a perspective view illustrating an example of a configuration of an accommodation case according to an embodiment of the disclosed technology.

Hereinafter, embodiments of the present invention will be described with reference to the drawings. In each of the drawings, substantially the same or equivalent configuration elements or parts are designated by the same reference numeral.

First Embodiment

Figure 1B:
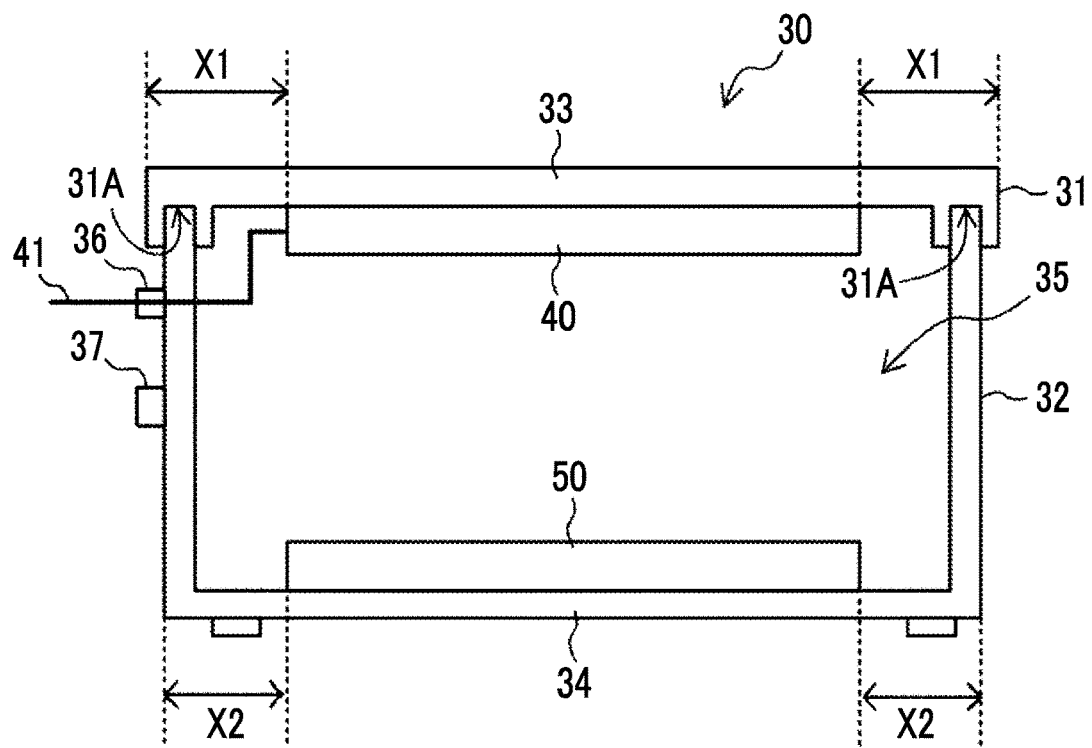
FIG. 1B is a cross-sectional view illustrating an example of a configuration of the accommodation case according to the embodiment of the disclosed technology.

FIG. 1A and FIG. 1B are respectively a perspective view and a cross-sectional view illustrating an example of a configuration of an accommodation case 30 according to the embodiment of the disclosed technology.

The accommodation case 30 includes a lid 31 having a first wall part 33, and a main body 32 having a second wall part 34 facing the first wall part 33. Further, the accommodation case 30 has an accommodation space 35 that is surrounded by a plurality of wall parts including the first wall part 33 and the second wall part 34. The first wall part 33 is arranged at the upper part of the accommodation space 35, and the second wall part 34 is arranged at the lower part of the accommodation space 35. The lid 31 is provided attachably and detachably with respect to the main body 32. The lid 31 and the main body 32 are made of, for example, an insulator such as plastic. The shape of the accommodation case 30 is not particularly limited; however, it is typically a rectangular parallelepiped shape.

The accommodation case 30 has a moisture-proof mechanism that suppresses the infiltration of aqueous moisture into the accommodation space 35. Specifically, the lid 31 has a groove 31A provided along the outer edge part thereof, and the upper end portion of the main body 32 is fitted into the groove 31A to seal the accommodation space 35, whereby it is suppressed that aqueous moisture infiltrates the inside of the accommodation space 35. A sealing member such as an O-ring, packing, or gasket may be provided at a portion where the lid 31 comes into contact with the main body 32 to enhance the moisture-proof function.

Further, the accommodation case 30 includes a power supply unit 40 that is provided on the first wall part 33 and a power reception unit 50 that is provided on the second wall part 34. More specifically, the power supply unit 40 is attached on the surface of the first wall part 33 on the side of the accommodation space 35, and the power reception unit 50 is attached on the surface of the second wall part 34 on the side of the accommodation space 35.

The power supply unit 40 is a wireless power supply unit that transmits electric power to a power supply destination in a noncontact state. As the electric power transmission method in the power supply unit 40, a magnetic field coupling method such as an electromagnetic coupling method or a magnetic field resonance method is applied. Accordingly, the power supply unit 40 has a configuration in which a power transmission coil (not illustrated in the drawing) is included. The wireless power supply by a magnetic field coupling method is a method of contactlessly transmitting electric power in which a power reception coil receives a magnetic field generated by a power transmission coil. As the power supply unit 40, for example, a power supply unit having an output of about 100 kHz to several hundred kHz and 5 W to 15 W according to the Qi standard is used. As the power supply destination of the power supply unit 40, as will be described later, a power reception unit that is provided in another accommodation case stacked on the accommodation case 30 is considered.

The power reception unit 50 is a wireless power reception unit that receives electric power that is supplied from a power supply source in a noncontact state. The electric power transmission method in the power reception unit 50 is the same as that in the power supply unit 40. The power reception unit 50 has a configuration in which a power reception coil (not illustrated in the drawing) that receives a magnetic field generated by a power transmission coil of a power supply source is included. As the power supply source that receives electric power supplied by the power reception unit 50, as will described later, a power supply unit that is provided in another accommodation case arranged under the accommodation case 30 or a power supply unit that is provided on a stage of an incubator, on which the accommodation case 30 is placed is considered.

The power supply unit 40 is arranged at a position spaced apart from the outer edge of the first wall part 33 by a predetermined distance X1. Similarly, the power reception unit 50 is arranged at a position spaced apart from the outer edge of the second wall part 34 by a predetermined distance X2. The distance X1 and the distance X2 are each preferably 10 mm or more.

The accommodation case 30 has a power supply port 36 for supplying electric power to the power supply unit 40. In a case where the power supply unit 40 receives electric power through the power supply port 36 and a power supply line 41, a current flows through a power transmission coil (not illustrated in the drawing), whereby a magnetic field is generated. In addition, the accommodation case 30 has an access port 37 for accessing an accommodated object that is accommodated in the inside of the accommodation space 35.

Figure 2:
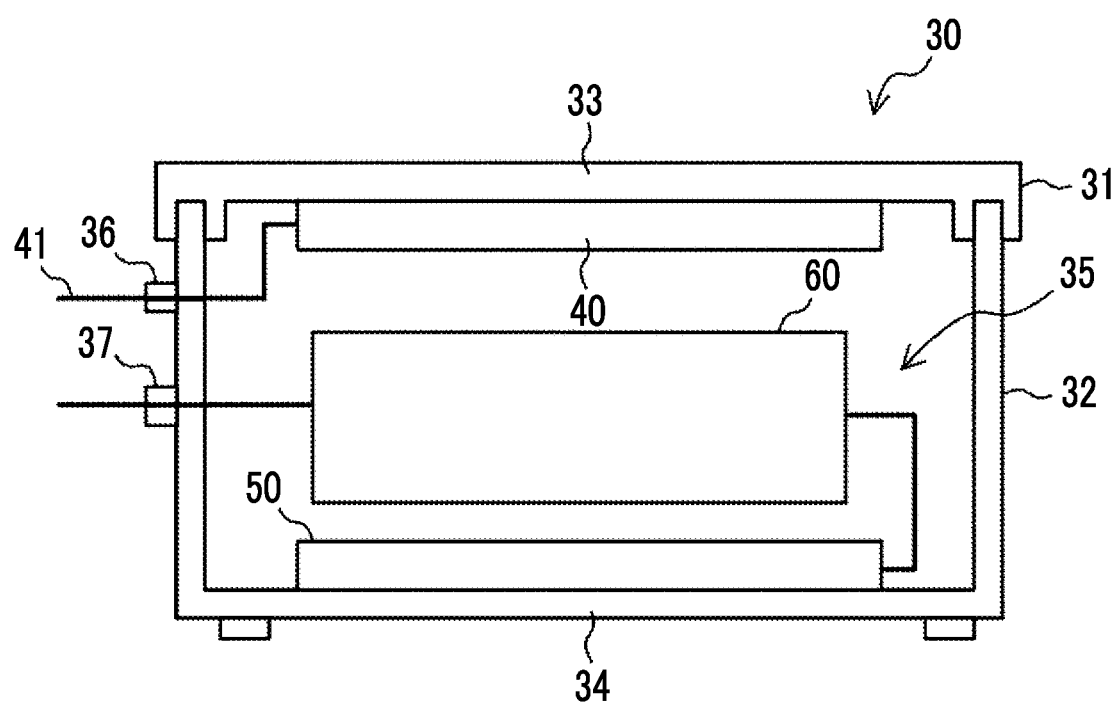
FIG. 2 is a view illustrating a state in which an electric device is accommodated in an accommodation space of the accommodation case according to the embodiment of the disclosed technology.

FIG. 2 is a view illustrating a state in which an electric device 60 is accommodated in the accommodation space 35 of the accommodation case 30. The electric device 60 that is accommodated in the accommodation case 30 is connected to the power reception unit 50 and can be operated by the electric power from the power reception unit 50. The access to the electric device 60 that is accommodated in the accommodation case 30 can be carried out through the access port 37 and an access line 80.

Figure 3:
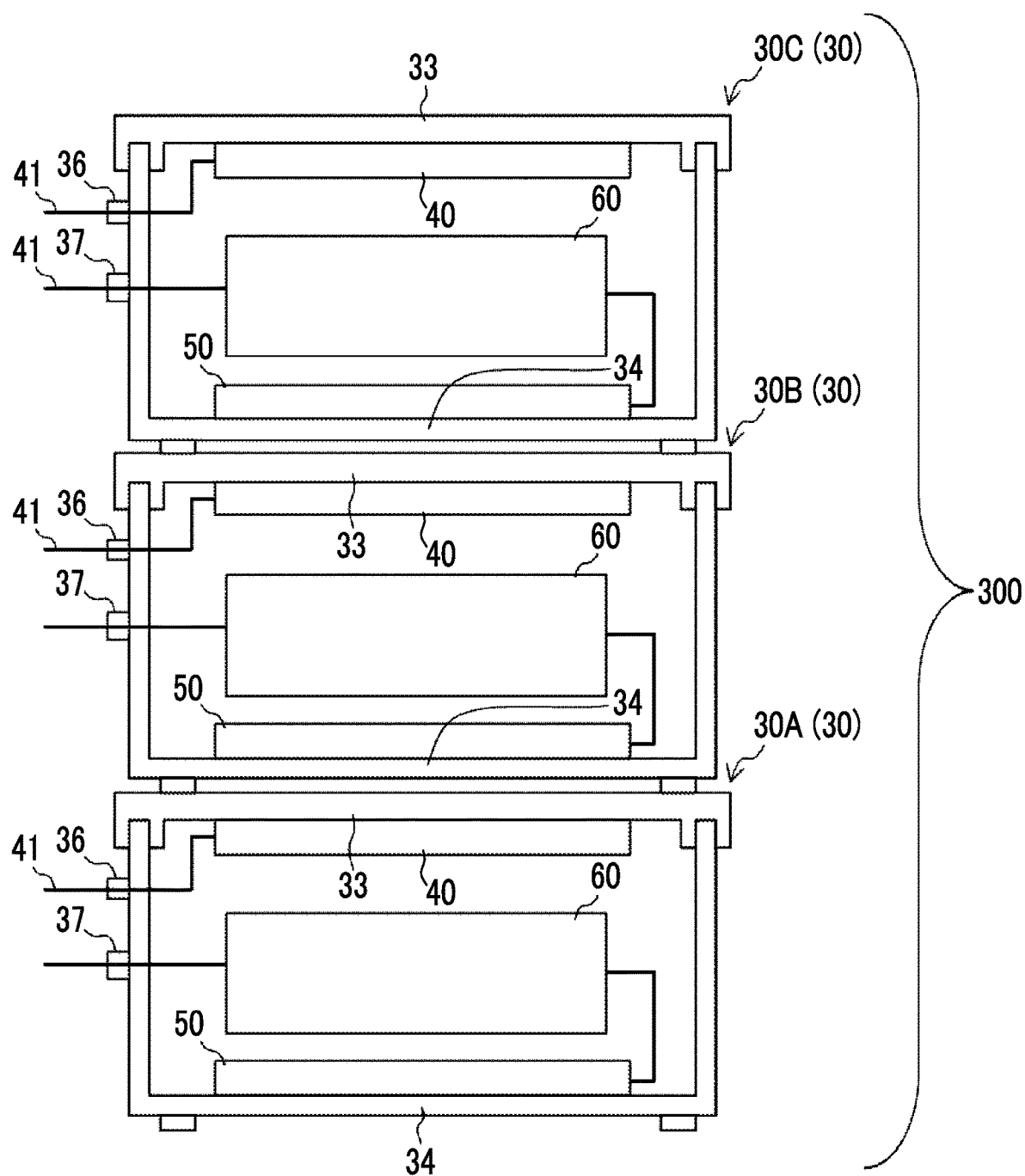
FIG. 3 is a view illustrating an example of a configuration of an accommodation case stack according to the embodiment of the disclosed technology.

FIG. 3 is a view illustrating an example of a configuration of an accommodation case stack 300 according to the embodiment of the disclosed technology. The accommodation case stack 300 has a configuration in which a plurality of accommodation cases 30 are stacked. In the example illustrated in FIG. 3, the accommodation case stack 300 having a configuration in which three accommodation cases 30 are stacked is exemplified; however, the number of accommodation cases 30 that constitute the accommodation case stack 300 can be appropriately increased or decreased. In FIG. 3, reference numerals 30A, 30B, and 30C are assigned to distinguish the three accommodation cases from each other.

An accommodation case 30B is stacked on an accommodation case 30A, and an accommodation case 30C is stacked on the accommodation case 30B. That is, the first wall part 33 of the accommodation case 30A and the second wall part 34 of the accommodation case 30B are adjacent to each other, and the first wall part 33 of the accommodation case 30B and the second wall part 34 of the accommodation case 30C are adjacent to each other.

Since the first wall part 33 of the accommodation case 30A and the second wall part 34 of the accommodation case 30B are adjacent to each other, the power supply unit 40 that is provided in the accommodation case 30A and the power reception unit 50 that is provided in the accommodation case 30B are adjacent to each other, and electric power can be transmitted between the power supply unit 40 that is provided in the accommodation case 30A and the power reception unit 50 that is provided in the accommodation case 30B with relatively high transmission efficiency. The electric device 60 that is accommodated in the accommodation case 30B is operated by receiving electric power that is supplied from the power reception unit 50 that is provided in the accommodation case 30B.

Since the first wall part 33 of the accommodation case 30B and the second wall part 34 of the accommodation case 30C are adjacent to each other, the power supply unit 40 that is provided in the accommodation case 30B and the power reception unit 50 that is provided in the accommodation case 30C are adjacent to each other, and electric power can be transmitted between the power supply unit 40 that is provided in the accommodation case 30B and the power reception unit 50 that is provided in the accommodation case 30C with relatively high transmission efficiency. The electric device 60 that is accommodated in the accommodation case 30C is operated by receiving electric power that is supplied from the power reception unit 50 that is provided in the accommodation case 30C.

The power reception unit 50 that is provided in the accommodation case 30A receives electric power that is supplied from, for example, a power supply unit that is provided on the stage of the incubator in which the accommodation case stack 300 is placed. The electric device 60 that is accommodated in the accommodation case 30A is operated by receiving electric power that is supplied from the power reception unit 50 that is provided in the accommodation case 30A.

In the accommodation case 30A that is arranged at the lowermost part, the power reception unit 50 may not be provided. In this case, an operation without accommodating the electric device 60 in the accommodation case 30A is considered. Further, in the accommodation case 30C that is arranged at the uppermost part, the power supply unit 40 may not be provided.

Figure 4:
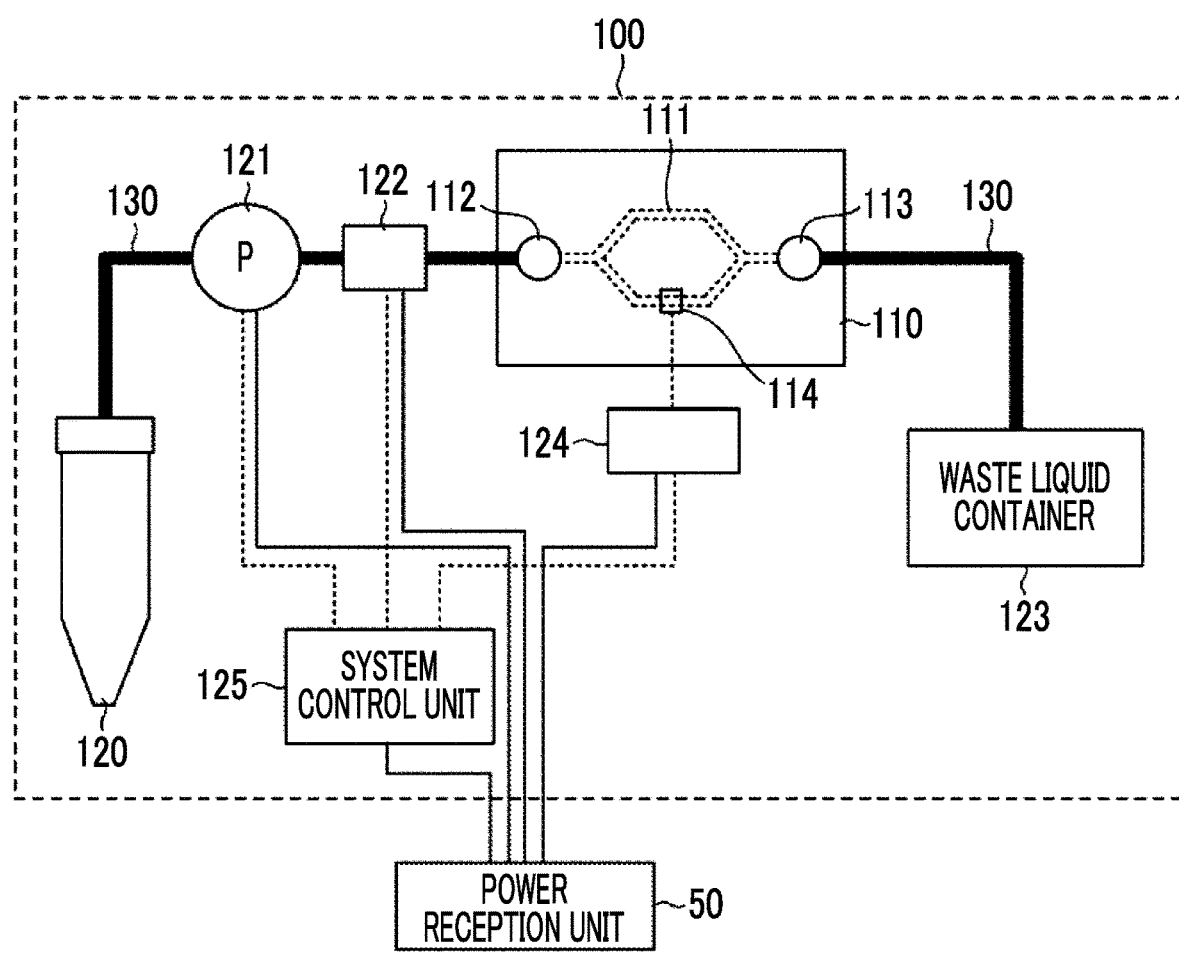
FIG. 4 is a view illustrating an example of a cell culture system according to the embodiment of the disclosed technology.

FIG. 4 is a view illustrating an example of a configuration of a cell culture system 100, in which a microfluidic device 110 is included. The cell culture system 100 has a configuration in which the microfluidic device 110, a storage container 120, a pump 121, a flow rate sensor 122, an impedance measuring instrument 124, a waste liquid container 123, a system control unit 125, and a pipe 130 are included.

The microfluidic device 110 has a micro flow channel 111 that is formed by using a microfabrication technology such as MEMS technology, an inflow port 112 that is provided at one end of the micro flow channel 111, and an outflow port 113 that is provided at the other end of the micro flow channel 111. Further, the microfluidic device 110 has an electrode 114 that is provided in the middle of the micro flow channel 111. In cell culture using the cell culture system 100, cells are arranged inside the micro flow channel 111, and then the cells are cultured.

The storage container 120 is connected to the inflow port 112 through the pipe 130. The pump 121 and the flow rate sensor 122 are provided in the middle of the pipe 130. The storage container 120 stores a liquid such as a medium, additives, and reagents, which is used for culturing cells accommodated in the microfluidic device 110. The cell culture system 100 may have a plurality of storage containers respectively storing a plurality of different kinds of liquids or may have a configuration such that liquids accommodated inside a plurality of storage containers can be selectively supplied to the microfluidic device 110.

The pump 121 carries out feeding of a liquid such as a medium stored in the storage container 120. In a case where the pump 121 is driven, the liquid accommodated in the storage container 120 is supplied to the micro flow channel 111 through the inflow port 112. The flow rate sensor 122 detects the flow rate of the liquid supplied to the microfluidic device 110 per unit time and outputs a detection signal indicating the detected flow rate. The liquid supplied to the micro flow channel 111 flows out from the outflow port 113 and is collected in the waste liquid container 123 through the pipe 130.

The impedance measuring instrument 124 is connected to the electrode 114 that is provided in the middle of the micro flow channel 111 and outputs an impedance value depending on the state of cells that are cultured on the micro flow channel 111 based on an electric signal supplied from the electrode 114. The above impedance value may correspond to, for example, a transepithelial electrical resistance value.

The system control unit 125 controls the drive of the pump 121 based on the detection signal output from the flow rate sensor 122. That is, the system control unit 125 controls the feeding amount of liquid in the pump 121 so that the flow rate of the liquid per unit time, which is indicated by the detection signal output from the flow rate sensor 122, becomes a predetermined value. Further, the system control unit 125 carries out control for recording the impedance value measured by the impedance measuring instrument 124 and transmitting it to the external system.

The electric device including the pump 121, the flow rate sensor 122, the impedance measuring instrument 124, and the system control unit 125 is operated by receiving electric power that is supplied from the power reception unit 50.

Figure 5:
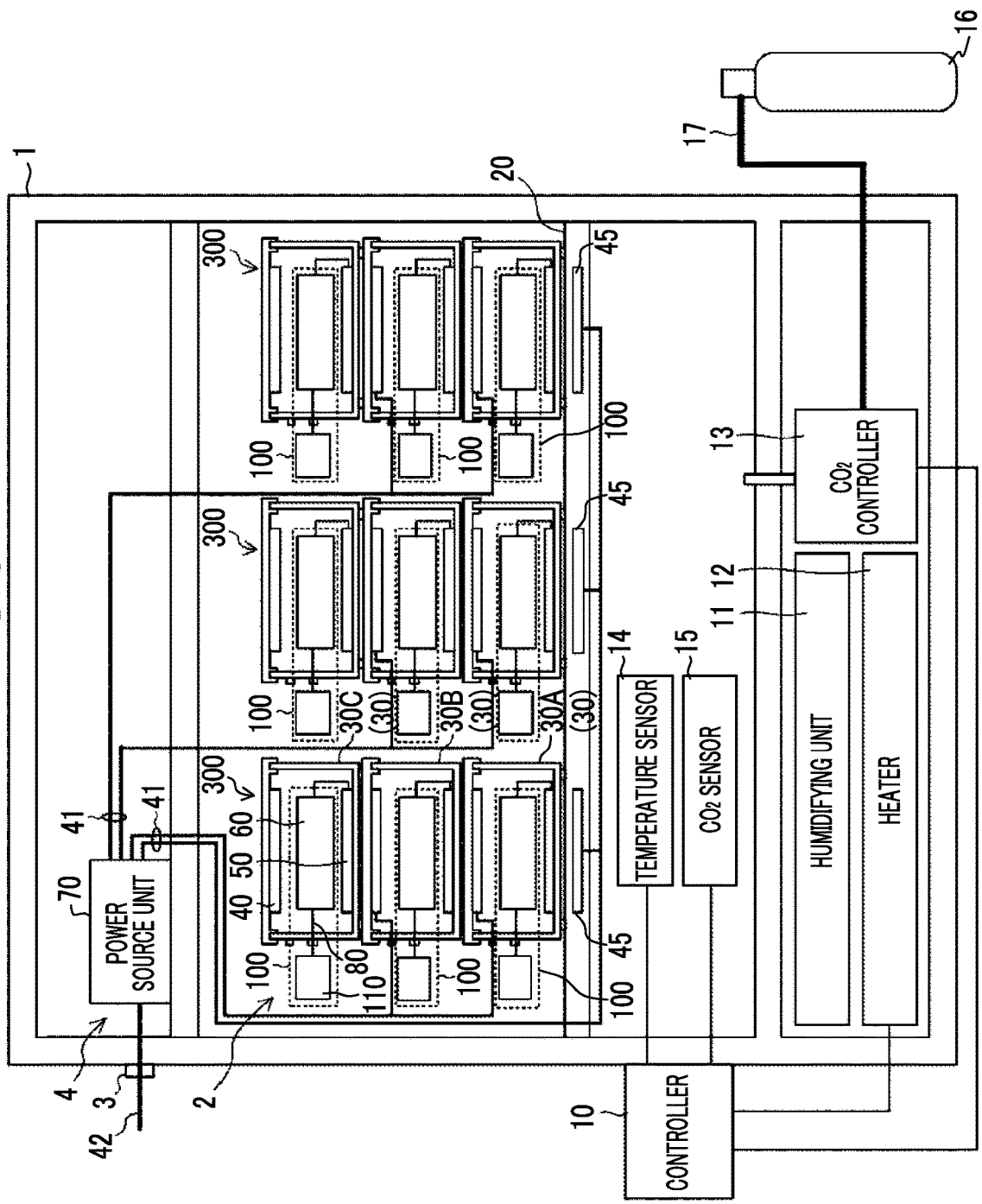
FIG. 5 is a view illustrating an example of a method of operating a microfluidic device according to the embodiment of the disclosed technology.

FIG. 5 is a view illustrating an example of a method of operating the microfluidic device 110. A plurality of cell culture systems 100 each including the microfluidic device 110 are accommodated inside an accommodation space 2 of an incubator 1.

The incubator 1 has the accommodation space 2 shielded from the external environment. The incubator 1 has a controller 10, a humidifying unit 11, a heater 12, a $CO_2$ controller 13, a temperature sensor 14, and a $CO_2$ sensor 15 as environmental control units for controlling the environment of the accommodation space 2.

The temperature sensor 14 is provided inside the accommodation space 2, detects the temperature in the accommodation space 2, and supplies a detection signal indicating the detected temperature to the controller 10. The $CO_2$ sensor 15 is provided inside the accommodation space 2, detects the $CO_2$ concentration in the accommodation space 2, and supplies a detection signal indicating the detected $CO_2$ concentration to the controller 10.

The controller 10 controls the heater 12 so that the temperature in the accommodation space 2 becomes the temperature specified by a user, based on the temperature detected by the temperature sensor 14. Further, the controller 10 controls the $CO_2$ controller 13 so that the $CO_2$ concentration in the accommodation space 2 becomes the concentration specified by a user, based on the $CO_2$ concentration detected by the $CO_2$ sensor 15. The $CO_2$ controller 13 is connected to a $CO_2$ cylinder 16, which is installed outside the incubator 1, through a pipe 17, and adjusts the amount of $CO_2$ gas that is released into the inside of the accommodation space 2 based on the control by the controller 10, where the $CO_2$ gas is supplied from the $CO_2$ cylinder 16.

The humidifying unit 11 has a configuration in which a vat in which water is stored is included, and the humidity in the accommodation space 2 is maintained above a predetermined value due to the spontaneous vaporization of the water in the vat.

A stage 20 is provided in the accommodation space 2. A plurality of power supply units 45 are provided on the stage 20. As each of the power supply units 45, the power supply unit the same as the power supply unit 40 that is provided in the accommodation case 30 is used.

On the stage 20, the accommodation case stacks 300 are arranged at positions matching with the respective power supply units 45. In the example illustrated in FIG. 5, each of the cell culture systems 100 corresponds to each of the accommodation cases 30. That is, one cell culture system 100 is disposed for one accommodation case 30. Each of the accommodation cases 30 constituting the accommodation case stack 300 accommodates the electric device 60 that includes a part or all of the pump 121, the flow rate sensor 122, the impedance measuring instrument 124, and the system control unit 125, among the configuration elements of the corresponding cell culture system 100. The microfluidic device 110 is connected to the electric device 60 that is accommodated in the corresponding accommodation case 30 through the access port 37 (see FIG. 3) and the access line 80. The storage container 120 and the waste liquid container 123, which are not illustrated in FIG. 5, are arranged outside the accommodation case 30 together with the microfluidic device 110.

Each of the power supply units 40 accommodated in the accommodation case 30 and each of the power supply units 45 provided on the stage 20 are connected to the power source unit 70 through the power supply line 41, and electric power is supplied from the power source unit 70, whereby a current flows to the power transmission coil (not illustrated in the drawing) to generate a magnetic field. In the example illustrated in FIG. 5, the power supply line 41 is not connected to the power supply units 40 that are provided in the accommodation case 30 at the uppermost part of the accommodation case stack 300, and thus electric power is not supplied to these power supply units 40.

The power source unit 70 is arranged in a shielded space 4 that is shielded from the accommodation space 2. The humidity in the shielded space 4 is set to be the same level as that of the humidity outside the incubator 1 and is lower than the humidity in the accommodation space 2 that is maintained at a relatively high humidity. Since the power source unit 70 is arranged in the shielded space 4, the power source unit 70 is prevented from being exposed to a high humidity environment, and the occurrence of problems such as electric leakage is suppressed. The power supply line 42 for supplying electric power to the power source unit 70 is led out to the outside of the incubator 1 through the power supply port 3 that is provided on the wall surface of the incubator 1. Here, in a case where the number of power supply lines that are led out to the outside of the incubator 1 is increased, the risk of foreign matters such as dust and bacteria being mixed into the inside of the accommodation space 2 of the incubator 1 increases. In a case where electric power is distributed from the power source unit 70 accommodated inside the incubator 1 to a plurality of power supply units 40 and power supply units 41 through the power supply line 41, the number of power supply lines that are led out to the outside of the incubator 1 can be reduced to one, and thus the risk of the inside of the accommodation space 2 being contaminated can be suppressed.

The power reception unit 50 that is provided in the accommodation case 30A arranged at the lowermost part of the accommodation case stack 300 receives electric power that is supplied from the power supply unit 45 that is provided on the stage 20. In a case where the electric device 60 that is accommodated in the accommodation case 30A arranged at the lowermost part of the accommodation case stack 300 is operated by receiving electric power that is supplied from the power reception unit 50 that is provided in the accommodation case 30A, whereby the above electric device 60 connected to the microfluidic device 110 is operated.

The power reception unit 50 that is provided in the accommodation case 30B stacked on the accommodation case 30A receives electric power that is supplied from the power supply unit 40 that is provided in the accommodation case 30A. In a case where the electric device 60 that is accommodated in the accommodation case 30B is operated by receiving electric power that is supplied from the power reception unit 50 that is provided in the accommodation case 30B, whereby the above electric device 60 connected to the microfluidic device 110 is operated.

The power reception unit 50 that is provided in the accommodation case 30C stacked on the accommodation case 30B receives electric power that is supplied from the power supply unit 40 that is provided in the accommodation case 30B. In a case where the electric device 60 that is accommodated in the accommodation case 30C is operated by receiving electric power that is supplied from the power reception unit 50 that is provided in the accommodation case 30C, whereby the above electric device 60 connected to the microfluidic device 110 is operated.

As described above, the first aspect of the method of operating the microfluidic device 110 according to the embodiment of the disclosed technology is realized by using the accommodation case 30. That is, the method of operating the microfluidic device 110 include accommodating the electric device 60 that is operated by receiving electric power that is supplied from the power reception unit 50, in the accommodation space 35 of the accommodation case 30, connecting the microfluidic device 110 to the electric device 60, and arranging the accommodation case in which the electric device 60 is accommodated and the microfluidic device 110 inside the incubator 1, to operate the microfluidic device 110.

In addition, the second aspect of the method of operating the microfluidic device 110 according to the embodiment of the disclosed technology is realized by using the accommodation case stack 300. That is, the method of operating the microfluidic device 110 includes accommodating a first electric device 60 that is operated by receiving electric power that is supplied from the power reception unit 50 that is provided in a first accommodation case 30, in the accommodation space 35 of the first accommodation case 30, accommodating a second electric device 60 that is operated by receiving electric power that is supplied from the power reception unit 50 that is provided in the second accommodation case 30, in the accommodation space 35 of the second accommodation case that is stacked on the first accommodation case 30, connecting the first microfluidic device 110 to the first electric device 60, connecting the second microfluidic device 110 to the second electric device 60, and arranging the first accommodation case 30 in which the first electric device 60 is accommodated, the second accommodation case 30 in which the second electric device 60 is accommodated, the first microfluidic device 110, and the second microfluidic device 110 inside the incubator 1, to operate the first microfluidic device 110 and the second microfluidic device 110.

According to the method of operating the accommodation case 30, the accommodation case stack 300, and the microfluidic device 110, according to the embodiment of the disclosed technology, electric power can be transmitted between the upper and lower accommodation cases adjacent to each other since a plurality of accommodation cases 30 are stacked. As a result, the degree of freedom in arranging the power reception unit 50 in the incubator 1 can be increased as compared with the case where the power supply unit is provided only in the stage 20 of the incubator 1. Therefore, it is possible to ensure a degree of freedom in arranging the electric devices 60 such as the sensor and the pump that are operated by receiving electric power that is supplied from the power reception unit 50.

Further, since the electric device 60 such as the sensor and the pump is accommodated in the accommodation case 30, the electric device 60 is not exposed to a high humidity environment in the incubator 1, and thus it is possible to suppress the risk of damaging electric devices due to moisture. In a case where the accommodation case 30 has a moisture-proof mechanism for preventing infiltration of aqueous moisture into the inside of the accommodation space 35, it is possible to enhance the effect of suppressing the risk of damage.

In addition, the power supply unit 40 is arranged at a position spaced apart from the outer edge of the first wall part 33, and the power reception unit 50 is arranged at a position spaced apart from the outer edge of the second wall part 34. As a result, as illustrated in FIG. 5, in a case where a plurality of accommodation case stacks 300 are arranged side by side on the stage 20, it is possible to ensure, in the plane direction, the distance between a power supply unit 40 that constitutes a certain accommodation case stack 300 and a power supply unit 40 that constitutes another adjacent accommodation case stack 300 and the distance between a power reception unit 50 that constitutes a certain accommodation case stack 300 and a power reception unit 50 that constitutes another adjacent accommodation case stack 300. As a result, it is possible to reduce the influence of the electromagnetic waves radiated from the power supply unit 40 and the power reception unit 50 on another power supply unit or power reception unit that is adjacent to the power supply unit 40 and the power reception unit 50 in the plane direction.

In the above embodiment, the case where each of the cell culture systems 100 is provided to correspond to each of the accommodation cases 30 is illustrated; however, the present invention is not limited to this aspect. That is, a plurality of electric devices constituting one cell culture system 100 may be dispersedly accommodated in a plurality of accommodation cases 30. In this case, in a case where a part or all of the plurality of electric devices dispersedly accommodated in the plurality of accommodation cases 30 are connected to the microfluidic device 110, the microfluidic device 110 is operated.

Further, in the above embodiment, a case where the power reception unit 50 is provided in the accommodation case 30A that is arranged at the lowermost part of the accommodation case stack 300, and the electric power supply to the power reception unit 50 is carried out by the power supply unit 45 that is provided on the stage 20; however, the present invention is not limited to this aspect. For example, the power supply unit 45 may not be provided on the stage 20. In this case, the power reception unit 50 may not be provided in the accommodation case 30A that is arranged at the lowermost part of the accommodation case stack 300, or the electric device 60 may not be accommodated in the accommodation case 30A. Further, in the accommodation case 30C that is arranged at the uppermost part of the accommodation case stack 300, the power supply unit 40 may not be provided.

Figure 6:
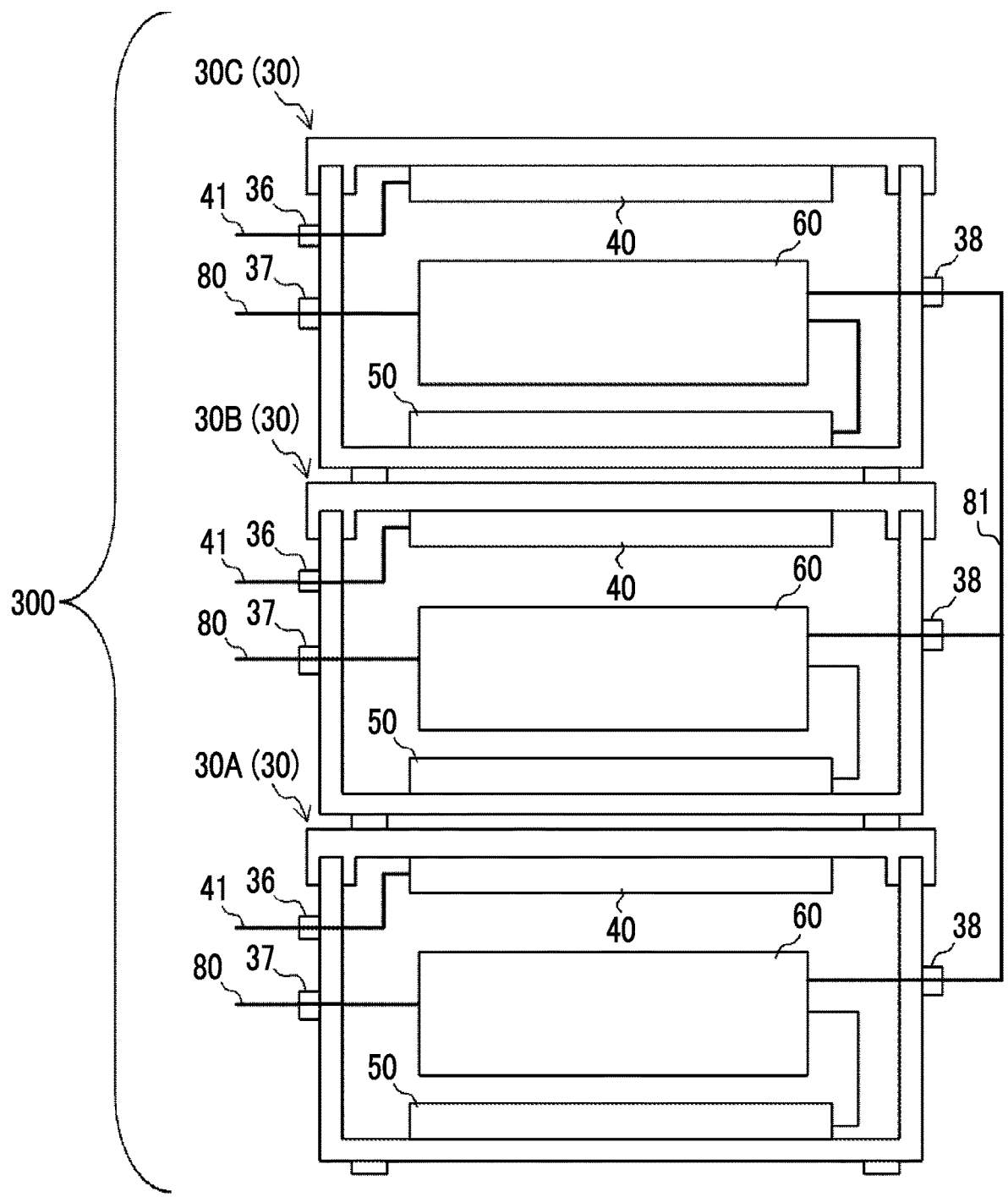
FIG. 6 is a view illustrating an example of a configuration of the accommodation case stack according to the embodiment of the disclosed technology.

Further, as illustrated in FIG. 6, the electric devices 60 that are accommodated in the accommodation cases 30 constituting the accommodation case stack 300 may be configured to communicate with each other through a communication port 38 and a communication line 81 that are provided in each of the accommodation cases 30.

Second Embodiment

Figure 7:
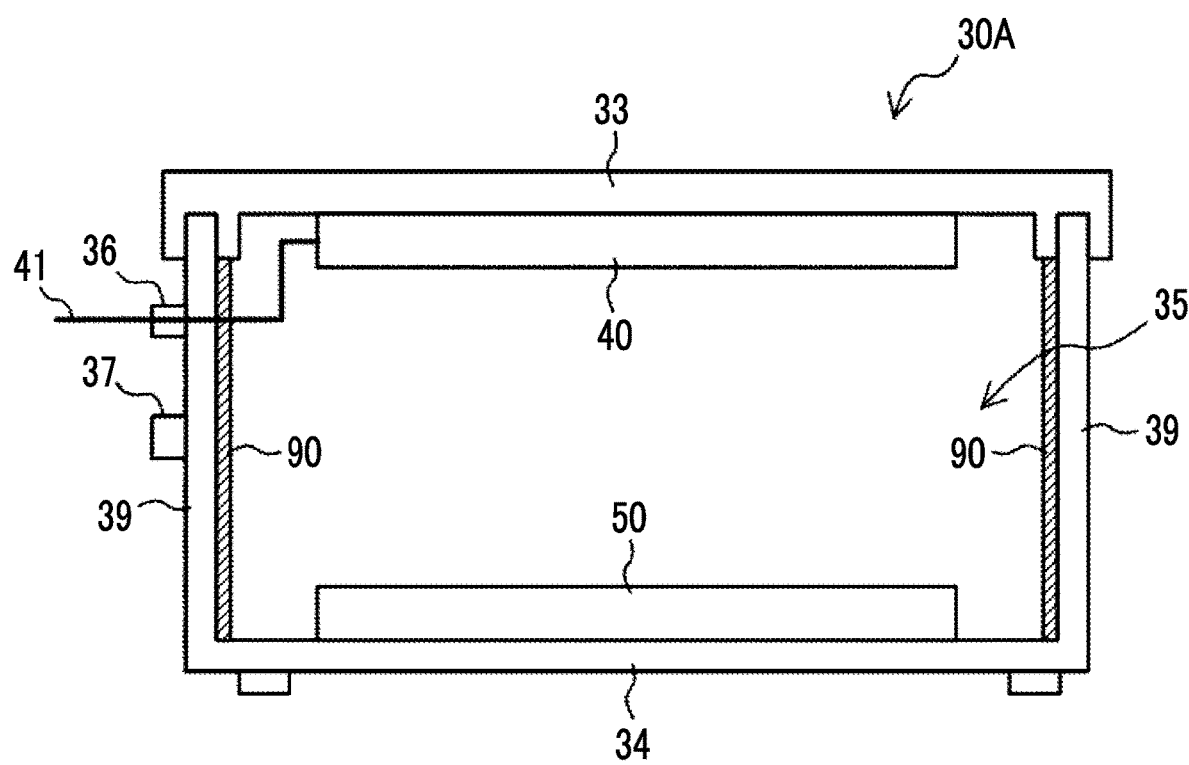
FIG. 7 is a cross-sectional view illustrating an example of a configuration of an accommodation case according to another embodiment of the disclosed technology.

FIG. 7 is a cross-sectional view illustrating an example of a configuration of the accommodation case 30A according to the second embodiment of the disclosed technology. In the accommodation case 30A, a wall part 39 surrounding the accommodation space 35 has a shielding part 90 that shields electromagnetic waves radiated from the power supply unit 40 and the power reception unit 50. The shielding part 90 can be made of, for example, a conductive film that covers the inner surface of the wall part 39. As the material of the conductive film, a metal such as aluminum, copper, or stainless steel can be used.

As described above, since the accommodation case 30A has the shielding part 90, it is possible to suppress the leakage of electromagnetic waves radiated from the power supply unit 40 and the power reception unit 50 to the outside of the accommodation case 30A. This makes it possible to suppress a risk that the electric device that is provided outside the accommodation case 30A malfunctions due to the electromagnetic waves radiated from the power supply unit 40 and the power reception unit 50.

The accommodation case stack 300 may have a configuration in which the accommodation case 30A according to the present embodiment is included. In addition, the electric device 60 that is operated by receiving electric power that is supplied from the power reception unit 50 may be accommodated in the accommodation space 35 of the accommodation case 30A according to the present embodiment, the microfluidic device 110 may be connected to the electric device 60, and the accommodation case 30A in which the electric device 60 is accommodated and the microfluidic device 110 may be arranged inside the incubator 1, to operate the microfluidic device 110.

The disclosure of JP2019-044497 filed on Mar. 12, 2019, is incorporated in the present specification in its entirety by reference. In addition, all documents, patent applications, and technical standards described in the present specification are incorporated in the present specification by reference, to the same extent as in the case where each of the documents, patent applications, and technical standards is specifically and individually described.

What is claimed is:

1. A method of operating a microfluidic device, which uses an accommodation case that includes:
   a first wall part in which a power supply unit that transmits electric power to a power reception unit in a noncontact state is provided,
   a second wall part in which the power reception unit, which receives electric power that is supplied from the power supply unit in a noncontact state, is provided, the second wall part facing the first wall part, and
   an accommodation space that is surrounded by a plurality of wall parts including the first wall part and the second wall part,
   the method comprising:
   accommodating an electric device that is operated by receiving electric power that is supplied from the power reception unit, in the accommodation space of the accommodation case;
   connecting the microfluidic device to the electric device; and
   arranging the accommodation case in which the electric device is accommodated and the microfluidic device in an incubator to operate the microfluidic device.

2. A method of operating a microfluidic device, which uses an accommodation case stack in which a first accommodation case and a second accommodation case are stacked, each of the first accommodation case and the second accommodation case including:
   a first wall part in which a power supply unit that transmits electric power to a power reception unit in a noncontact state is provided,
   a second wall part in which the power reception unit, which receives electric power that is supplied from the power supply unit in a noncontact state, is provided, the second wall part facing the first wall part, and
   an accommodation space that is surrounded by a plurality of wall parts including the first wall part and the second wall part, wherein the first wall part of the first accommodation case and the second wall part of the second accommodation case are adjacent to each other, the method comprising:

accommodating a first electric device that is operated by receiving electric power that is supplied from the power reception unit that is provided on the second wall part of the first accommodation case, in the accommodation space of the first accommodation case;

accommodating a second electric device that is operated by receiving electric power that is supplied from the power reception unit that is provided on the second wall part of the second accommodation case, in the accommodation space of the second accommodation case;

connecting a first microfluidic device to the first electric device;

connecting a second microfluidic device to the second electric device; and arranging the first accommodation case in which the first electric device is accommodated, the second accommodation case in which the second electric device is accommodated, the first microfluidic device, and the second microfluidic device in an incubator to operate the first microfluidic device and the second microfluidic device.

3. The method of operating a microfluidic device according to claim 2,
wherein the first electric device communicates with the second electric device.

4. The method of operating a microfluidic device according to claim 1, wherein the accommodation case also includes a moisture-proof mechanism for preventing infiltration of aqueous moisture into the accommodation space.

5. The method of operating a microfluidic device according to claim 1, wherein:

the first wall part is arranged in an upper part of the accommodation space, and the second wall part is arranged in a lower part of the accommodation space.

6. The method of operating a microfluidic device according to claim 1, wherein:

the power supply unit is arranged at a position spaced apart from an outer edge of the first wall part, and the power reception unit is arranged at a position spaced apart from an outer edge of the second wall part.

7. The method of operating a microfluidic device according to claim 1, wherein at least one of the plurality of wall parts has a shielding part that shields electromagnetic waves radiated from the power supply unit and the power reception unit.

8. The method of operating a microfluidic device according to claim 1, further comprising an access port for accessing an accommodated object that is accommodated in the accommodation space.

\* \* \* \* \*